United States Patent
Mannoh et al.

(10) Patent No.: US 11,589,801 B2
(45) Date of Patent: Feb. 28, 2023

(54) METHODS AND APPARATUS FOR INTRAOPERATIVE ASSESSMENT OF PARATHYROID GLAND VASCULARITY USING LASER SPECKLE CONTRAST IMAGING AND APPLICATIONS OF SAME

(71) Applicant: Vanderbilt University, Nashville, TN (US)

(72) Inventors: Emmanuel A. Mannoh, Nashville, TN (US); Anita Mahadevan-Jansen, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 916 days.

(21) Appl. No.: 16/471,049

(22) PCT Filed: Dec. 29, 2017

(86) PCT No.: PCT/US2017/068907
§ 371 (c)(1),
(2) Date: Jun. 19, 2019

(87) PCT Pub. No.: WO2018/126114
PCT Pub. Date: Jul. 5, 2018

(65) Prior Publication Data
US 2019/0328309 A1    Oct. 31, 2019

Related U.S. Application Data

(63) Continuation-in-part of application No. 15/391,046, filed on Dec. 27, 2016, now Pat. No. 10,258,275.
(Continued)

(51) Int. Cl.
G01B 11/24 (2006.01)
A61B 5/00 (2006.01)
(Continued)

(52) U.S. Cl.
CPC ............ *A61B 5/415* (2013.01); *A61B 5/0071* (2013.01); *A61B 5/0075* (2013.01);
(Continued)

(58) Field of Classification Search
CPC ..... A61B 5/415; A61B 5/0071; A61B 5/0075; A61B 5/0086; A61B 5/418; A61B 5/4227;
(Continued)

(56) References Cited

U.S. PATENT DOCUMENTS

| 2006/0278240 A1 | 12/2006 | Spillman et al. |
| 2012/0010483 A1 | 1/2012 | Mahadevan-Jansen et al. |
| 2014/0163391 A1 | 6/2014 | Koizumi et al. |

FOREIGN PATENT DOCUMENTS

| WO | 2009008745 A2 | 1/2009 |
| WO | 2012096878 A2 | 7/2012 |
| WO | 2015176294 A1 | 11/2015 |

OTHER PUBLICATIONS

European Patent Office (ISR/KR), "Extended EP Search Report for EP Application No. 178888956", The Hague, dated Jul. 22, 2020.
(Continued)

*Primary Examiner* — Md M Rahman
(74) *Attorney, Agent, or Firm* — Locke Lord LLP; Tim Tingkang Xia, Esq.

(57) ABSTRACT

One aspect of the invention relates to a method for intraoperative assessment of parathyroid gland viability in a surgery. The method includes diffusing a beam of light onto a tissue surface of a parathyroid gland of a patient to illuminate the tissue surface; acquiring images of the illuminated tissue surface, where each of the acquired images includes a speckle pattern; and processing the acquired images to obtain speckle contrast images for the intraoperative assessment of parathyroid gland viability.

22 Claims, 7 Drawing Sheets

Related U.S. Application Data

(60) Provisional application No. 62/440,112, filed on Dec. 29, 2016, provisional application No. 62/540,767, filed on Aug. 3, 2017.

(51) Int. Cl.
    *G01N 21/65* (2006.01)
    *G01N 21/64* (2006.01)
    *A61B 34/20* (2016.01)

(52) U.S. Cl.
    CPC ............ *A61B 5/0086* (2013.01); *A61B 5/418* (2013.01); *A61B 5/4227* (2013.01); *A61B 5/742* (2013.01); *A61B 34/20* (2016.02); *G01N 21/6456* (2013.01); *G01N 21/65* (2013.01); *A61B 2034/2055* (2016.02); *A61B 2505/05* (2013.01); *G01N 2021/6439* (2013.01); *G01N 2201/0221* (2013.01)

(58) Field of Classification Search
    CPC . A61B 5/742; A61B 34/20; A61B 2034/2055; A61B 2505/05; A61B 5/0261; G01N 21/6456; G01N 21/65; G01N 2021/6439; G01N 2201/0221; G01N 2021/4764; G01N 2021/479; G01N 2201/0634
    USPC .......................................................... 356/602
    See application file for complete search history.

(56) References Cited

OTHER PUBLICATIONS

McWade, M. et al., "Development of an Intraoperative Tool To Detect Parathyroid Gland Autofluorescence", https://etd.library.vanderbilt.edu/available/etd-04152016-131447/unrestricted/McWade.pdf, May 2016, Nashville, Tennessee.
Heller, Sherman et al., "Nuclear Probes and Intraoperative Gamma Cameras", Seminars in Nclear Medicine, No. 41, No. 3, Dec. 4, 2010, pp. 166-181.
Mannoh, E. A. et al., "Intraoperative Assessment of Parathyroid Viability using Laser Speckle Contrast Imaging", Scientific Reports, vol. 7, No. 1, Nov. 1, 2017.
American Thyroid Association. General Information/Press Room. (2017). At http://www.thyroid.org/media-main/press-room/.
Sun, G. H., DeMonner, S. & Davis, M. M. Epidemiological and Economic Trends in Inpatient and Outpatient Thyroidectomy in the United States, 1996-2006. Thyroid 23, 727-733 (2013).
Rafferty, M. A. et al. Completion Thyroidectomy Versus Total Thyroidectomy: Is There a Difference in Complication Rates? An Analysis of 350 Patients. J. Am. Coll. Surg. 205, 602-607 (2007).
Schwartz, A. E. & Friedman, E. W. Preservation of the parathyroid glands in total thyroidectomy. Surg. Gynecol. Obstet. 165, 327-32 (1987).
Ritter, K., Elfenbein, D., Schneider, D. F., Chen, H. & Sippel, R. S. Hypoparathyroidism after total thyroidectomy: incidence and resolution. J. Surg. Res. 197, 348-53 (2015).
Demeester-Mirkine, N., Hooghe, L., Van Geertruyden, J. & De Maertelaer, V. Hypocalcemia after thyroidectomy. Arch. Surg. 127, 854-8 (1992).
Pattou, F. et al. Hypocalcemia following Thyroid Surgery: Incidence and Prediction of Outcome. World J. Surg 22, 718-724 (1998).
McHenry, C. R., Speroff, T., Wentworth, D. & Murphy, T. Risk factors for postthyroidectomy hypocalcemia. Surgery 116, 641-7-8 (1994).
Zahedi Niaki, N. et al. The Cost of Prolonged Hospitalization due to Postthyroidectomy Hypocalcemia: A Case-Control Study. Adv. Endocrinol. 2014, 1-4 (2014).
Naveh-Many, T. "Development of Parathyroid Glands". Molecular Biology of the Parathyroid. 1-2 (Landes Bioscience / Eurekah.com, 2005).
Mohebati, A. & Shaha, A. R. Anatomy of thyroid and parathyroid glands and neurovascular relations. Clin. Anat. 25,19-31 (2012).
Lo, C. Y. et al. Parathyroid Autotransplantation During Thyroidectomy. Arch. Surg. 136, 1381 (2001).
Sierra, M. et al. Prospective biochemical and scintigraphic evaluation of autografted normal parathyroid glands in patients undergoing thyroid operations. Surgery 124, 1005-10 (1998).
Kuriloff, D. B. & Kizhner, V. Parathyroid gland preservation and selective autotransplantation utilizing topical lidocaine in total thyroidectomy. Laryngoscope 120, 1342-1344 (2010).
Ezzat, W. et al. Intraoperative parathyroid hormone as an indicator for parathyroid gland preservation in thyroid surgery. Swiss Med. Wkly. (2011). doi:10.4414/smw.2011.13299.
Fortuny, J. V. et al. Parathyroid gland angiography with indocyanine green fluorescence to predict parathyroid function after thyroid surgery. Br. J. Surg. 103, 537-543 (2016).
Boas, D. A. & Dunn, A. K. Laser speckle contrast imaging in biomedical optics. J. Biomed. Opt. 15, 11109 (2010).
Choi, B., Kang, N. M. & Nelson, J. S. Laser speckle imaging for monitoring blood flow dynamics in the in vivo rodent dorsal skin fold model. Microvasc. Res. 68, 143-6 (2004).
Iredahl, F., Löfberg, A., Sjoberg, F., Farnebo, S. & Tesselaar, E. Non-Invasive Measurement of Skin Microvascular Response during Pharmacological and Physiological Provocations. PLoS One 10, e0133760 (2015).
Dunn, A. K., Bolay, H., Moskowitz, M. A. & Boas, D. A. Dynamic Imaging of Cerebral Blood Flow Using Laser Speckle. J. Cereb. Blood Flow Metab. 21, 195-201 (2001).
Huang, Y.-C., Ringold, T. L., Nelson, J. S. & Choi, B. Noninvasive blood flow imaging for real-time feedback during laser therapy of port wine stain birthmarks. Lasers Surg. Med. 40, 167-173 (2008).
Mirdell, R., Iredahl, F., Sj?berg, F., Farnebo, S. & Tesselaar, E. Microvascular blood flow in scalds in children and its relation to duration of wound healing: A study using laser speckle contrast imaging. Burns 42, 648-654 (2016).
Richards, L. M. et al. Intraoperative multi-exposure speckle imaging of cerebral blood flow. J. Cereb. Blood Flow Metab. 0271678X1668698 (2017). doi:10.1177/0271678X16686987.
Sexton, K. J., Zhao, Y., Davis, S. C., Jiang, S. & Pogue, B. W. Optimization of fluorescent imaging in the operating room through pulsed acquisition and gating to ambient background cycling. Biomed. Opt. Express 8, 2635 (2017).
Kirkpatrick, S. J., Duncan, D. D. & Wells-Gray, E. M. Detrimental effects of speckle-pixel size matching in laser speckle contrast imaging. Opt. Lett. 33, 2886 (2008).
Korean Intellectual Property Office (ISR/KR), "International Search Report for PCT/US2017/068907", Korea, dated Jul. 17, 2018.

METHODS AND APPARATUS FOR INTRAOPERATIVE ASSESSMENT OF PARATHYROID GLAND VASCULARITY USING LASER SPECKLE CONTRAST IMAGING AND APPLICATIONS OF SAME

CROSS-REFERENCE TO RELATED PATENT APPLICATIONS

This PCT application claims priority to and the benefit of, U.S. Provisional Application Ser. No. 62/440,112, filed Dec. 29, 2016, entitled "LASER SPECKLE IMAGE FOR INTRAOPERATIVE DETECTION OF PARATHYROID GLAND VIABILITY AND APPLICATIONS OF SAME," by Emmanuel A. Mannoh et al. and U.S. Provisional Application Ser. No. 62/540,767, filed Aug. 3, 2017, entitled "METHODS AND SYSTEMS FOR INTRAOPERATIVE ASSESSMENT OF PARATHYROID GLAND VASCULARITY USING LASER SPECKLE CONTRAST IMAGING AND APPLICATIONS OF SAME," by Emmanuel A. Mannoh et al., which are incorporated herein in their entireties by reference.

This PCT application is a continuation-in-part application of U.S. application Ser. No. 15/391,046, filed Dec. 27, 2016, entitled "INTRA-OPERATIVE USE OF FLUORESCENCE SPECTROSCOPY AND APPLICATIONS OF SAME", by Anita Mahadevan-Jansen et al., which is incorporated herein in its entirety by reference.

Some references, which may include patents, patent applications, and various publications, are cited and discussed in the description of the present invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, [n] represents the nth reference cited in the reference list. For example, [2] represents the second reference cited in the reference list, namely, Sun, G. H., DeMonner, S. & Davis, M. M. Epidemiological and Economic Trends in Inpatient and Outpatient Thyroidectomy in the United States, 1996-2006. *Thyroid* 23, 727-733 (2013).

STATEMENT AS TO RIGHTS UNDER FEDERALLY-SPONSORED RESEARCH

This invention was made with government support under Contract No. 9R42CA192243-03 awarded by the National Institutes of Health (NIH). The government has certain rights in the invention.

FIELD OF THE INVENTION

The present invention relates generally to optical assessments of bio-objects, and more particularly to methods and apparatus/systems for intraoperative assessment of parathyroid gland vascularity using laser speckle contrast imaging and applications of the same.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

Approximately 8 million Americans are diagnosed annually with some form of thyroid disease [1], over 92,000 of whom undergo partial or total thyroidectomy as definitive treatment [2]. An estimated 3% of these procedures result in the patient being permanently unable to produce sufficient levels of parathyroid hormone for normal serum calcium regulation [3, 4]. Additionally, a significant proportion of patients suffer from a transient form of this post-surgical hypoparathyroidism and consequent hypocalcemia [5-8], with some studies reporting incidences as high as 47% [8]. Hypocalcemia can lead to cardiac arrhythmias, muscle spasms, tetany and eventually death, and is a huge economic burden for these patients who may require extended hospital stays or have to take regular calcium supplements for the rest of their lives to prevent these effects [9]. It is also one of the main causes for malpractice lawsuits after endocrine surgery [7]. Post-surgical hypoparathyroidism results from accidental disruption of the blood supply to, or accidental removal of, otherwise healthy parathyroid glands, organs responsible for regulating calcium. There are typically four parathyroid glands, which contain calcium-sensing receptors and secrete parathyroid hormone (PTH) in response to low serum calcium. Parathyroid hormone acts on bone to promote resorption, on the kidneys to reduce calcium elimination in urine, and on the intestines to promote calcium absorption through the intestinal wall, all of which help to increase serum calcium [10]. Vascular compromise of parathyroid glands may occur after thyroidectomy because of the close proximity of the parathyroid glands to the thyroid. In many cases, the parathyroid glands derive their blood supply from the same blood vessels that feed the thyroid [11]. Fortunately, devascularized parathyroid glands can be salvaged by autotransplantation—a procedure by which the gland is excised and transplanted typically into the sternocleidomastoid muscle [12]. However, identifying these glands is challenging and currently depends on subjective visual assessment and surgeon experience. Additionally, failure to revive parathyroid function after autotransplantation has been reported to occur in 14-17% of cases [12, 13]. As a result, a surgeon needs to be certain that a parathyroid gland is devascularized, and therefore not viable if left in place, before committing to this procedure.

A number of techniques have been employed to assess parathyroid viability, intraoperatively. A common approach is to look for bright red bleeding after pricking the parathyroid gland with a needle or cutting off tiny fragments [14], however care needs to be taken not to irreversibly damage the gland. Topical application of a dilute lidocaine solution has been employed to cause vasodilation in vascularized parathyroid glands. Any gland that does not swell after application of lidocaine is considered not viable and is therefore autotransplanted. This procedure is risky, since lidocaine can cause paralysis of the vocal cords if it comes into contact with the exposed laryngeal nerve [14]. Intraoperative measurement of PTH is performed routinely in parathyroidectomies to confirm removal of the hyperactive gland. Since the half-life of PTH in the blood is 3-5 minutes, removal of a parathyroid gland leads to noticeable decrease in serum PTH within a relatively short amount of time. Based on this concept, intraoperative measurement of PTH has also been employed in thyroidectomies [15], however this approach gives no indication of which parathyroid gland might be compromised. Another approach is to use indocyanine green (ICG) angiography to identify devascularized parathyroid glands. One study reported that hypoparathyroidism did not occur after surgery in thyroidectomy patients where at least one parathyroid gland was determined (by qualitative assessment of ICG fluorescence) to be well vascularized [16]. This method requires administration of an exogenous contrast agent and is limited by how frequently it can be performed.

Therefore, there is a critical need for a real-time, contrast-free and objective method for assessing the viability of parathyroid glands intraoperatively.

SUMMARY OF THE INVENTION

One of the objectives of this invention is to evaluate the capability of laser speckle contrast imaging (LSCI) to distinguish between vascularized and compromised parathyroid glands as determined by an experienced surgeon, in real-time during an endocrine surgery.

In one aspect, the invention relates to a method for intraoperative assessment of parathyroid gland viability in a surgery. In one embodiment, the method includes diffusing a beam of light onto a tissue surface of a parathyroid gland of a patient to illuminate the tissue surface; acquiring images of the illuminated tissue surface, where each of the acquired images comprises a speckle pattern; and processing the acquired images to obtain speckle contrast images for the intraoperative assessment of parathyroid gland viability.

In one embodiment, the method further includes displaying the speckle contrast images of the parathyroid gland in real-time.

In one embodiment, the beam of light is emitted from a light source. In one embodiment, the light source comprises an infrared laser.

In one embodiment, said acquiring the images of the illuminated tissue surface is performed with a detector.

In one embodiment, the detector comprises a camera. In one embodiment, the camera comprises an infrared camera or a near-infrared camera. In one embodiment, the detector further comprises a focus tunable lens attached to the front end of the camera.

In one embodiment, in the speckle contrast images, a perfused parathyroid gland has low speckle contrast, and a devascularized parathyroid gland has high speckle contrast.

In one embodiment, said processing the acquired images comprises calculating a plurality of speckle contrasts from the acquired images of the parathyroid gland.

In one embodiment, said calculating plurality of speckle contrasts comprises defining a window with a number of pixels over which a speckle contrast is to be calculated; moving the window across the acquired image of the speckle pattern; and at each location, calculating the speckle contrast as a standard deviation of pixel intensity values $\sigma_s$ within the window divided by a mean intensity value $\langle I \rangle$ as follows:

$$K_s = \frac{\sigma_s}{\langle I \rangle}$$

where the resultant speckle contrast image has values that range from 0 to 1, with values closer to 0 representing regions of greater motion (perfusion) and 1 representing regions with no motion.

In another aspect, the invention relates to an apparatus for intraoperative assessment of parathyroid gland viability in a surgery. In one embodiment, the apparatus includes a light source for emitting a beam of light; a diffuser coupled to the light source for diffusing the beam of light onto a tissue surface of a parathyroid gland of a patient to illuminate the tissue surface; a detector for acquiring images of the illuminated tissue surface, where each of the acquired images comprises a speckle pattern; and a controller arranged to operate the detector to acquire the images of the illuminated tissue surface, receive the acquired images from the detector, and process the acquired images to obtain speckle contrast images for the intraoperative assessment of parathyroid gland viability.

In one embodiment, the apparatus further includes a laser pointer arranged in relation to the detector such that its beam is co-localized with a center of the field of view of the detector at a distance.

In one embodiment, the apparatus further includes a display for displaying the speckle contrast images of the parathyroid gland in real-time.

In one embodiment, the light source comprises an infrared laser.

In one embodiment, the diffuser comprises a biconvex lens.

In one embodiment, the detector comprises a camera. In one embodiment, the camera comprises an infrared camera or a near-infrared camera. In one embodiment, the detector further comprises a focus tunable lens attached to the front end of the camera.

In one embodiment, in the speckle contrast images, a perfused parathyroid gland has low speckle contrast, and a devascularized parathyroid gland has high speckle contrast.

In one embodiment, said processing the acquired images of the parathyroid gland by the controller is performed with calculating a plurality of speckle contrasts from the acquired images of the parathyroid gland.

In one embodiment, said calculating a plurality of speckle contrasts from the acquired images of the parathyroid gland is performed by defining a window with a number of pixels over which a speckle contrast is to be calculated; moving the window across the acquired image of the speckle pattern; and at each location, calculating the speckle contrast as a standard deviation of pixel intensity values $\sigma_s$ within the window divided by a mean intensity value $\langle I \rangle$ as follows:

$$K_s = \frac{\sigma_s}{\langle I \rangle}$$

where the resultant speckle contrast image has values that range from 0 to 1, with values closer to 0 representing regions of greater motion (perfusion) and 1 representing regions with no motion.

In yet another aspect, the invention relates to a method for intraoperative detection of parathyroid gland viability in a surgery. In one embodiment, the method comprises obtaining speckle contrast images of a parathyroid gland of a patent; and displaying the speckle contrast images of the parathyroid gland in real-time.

In one embodiment, said obtaining the speckle contrast images of the parathyroid gland of the patent comprises diffusing a beam of light onto a tissue surface of a parathyroid gland of a patient to illuminate the tissue surface; acquiring images of the illuminated tissue surface, where each of the acquired images comprises a speckle pattern; and processing the acquired images to obtain speckle contrast images.

In one embodiment, in the speckle contrast images, a perfused parathyroid gland has low speckle contrast, and a devascularized parathyroid gland has high speckle contrast.

In one embodiment, said processing the acquired images comprises calculating a plurality of speckle contrasts from the acquired images of the parathyroid gland.

In one embodiment, said calculating plurality of speckle contrasts comprises defining a window with a number of pixels over which a speckle contrast is to be calculated; moving the window across the acquired image of the speckle pattern; and at each location, calculating the speckle contrast as a standard deviation of pixel intensity values as within the window divided by a mean intensity value $\langle I \rangle$ as follows:

$$K_s = \frac{\sigma_s}{\langle I \rangle}$$

where the resultant speckle contrast image has values that range from 0 to 1, with values closer to 0 representing regions of greater motion (perfusion) and 1 representing regions with no motion.

In a further aspect, the invention relates to an apparatus for intraoperative detection of parathyroid gland viability in a surgery. In one embodiment, the apparatus has means for obtaining speckle contrast images of a parathyroid gland of a patent; and displaying the speckle contrast images of the parathyroid gland in real-time.

In one embodiment, said means for obtaining the speckle contrast images comprises a light source for emitting a beam of light that is diffused onto a tissue surface of the parathyroid gland of the patient to illuminate the tissue surface; a detector for acquiring images of the illuminated tissue surface; and a controller arranged to operate the detector to acquire the images of the illuminated tissue surface, receive the acquired images from the detector, and process the acquired images to obtain the speckle contrast images.

In one embodiment, the light source comprises an infrared laser.

In one embodiment, the beam of light is diffused onto the tissue surface of the parathyroid gland by a diffuser including a biconvex lens.

In one embodiment, the detector comprises a camera. In one embodiment, the camera comprises an infrared camera or a near-infrared camera. In one embodiment, the detector further comprises a focus tunable lens attached to the front end of the camera.

In one embodiment, in the speckle contrast images, a perfused parathyroid gland has low speckle contrast, and a devascularized parathyroid gland has high speckle contrast.

These and other aspects of the present invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The accompanying drawings form part of the present specification and are included to further demonstrate certain aspects of the invention. The invention may be better understood by reference to one or more of these drawings in combination with the detailed description of specific embodiments presented herein. The drawings described below are for illustration purposes only. The drawings are not intended to limit the scope of the present teachings in any way.

DETAILED DESCRIPTION OF THE INVENTION

Figure 1:
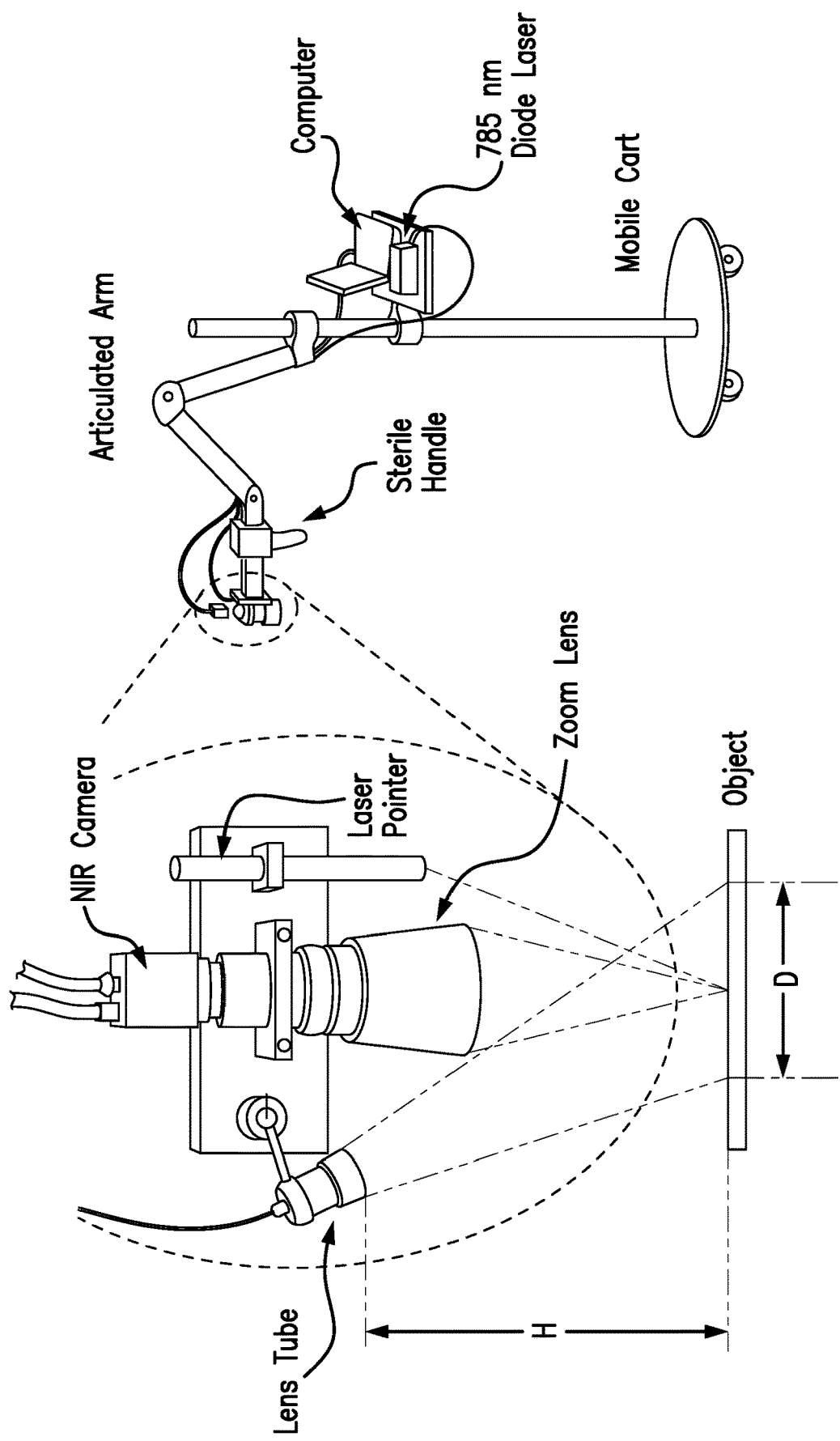
FIG. 1 shows schematically a laser speckle contrast imaging (LSCI) device for intraoperative assessment of parathyroid gland according to one embodiment of the invention.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this invention is thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It is appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It is understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It is understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It is understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It are also appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It is further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It is understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It is further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

Embodiments of the invention are illustrated in detail hereinafter with reference to accompanying drawings. It should be understood that specific embodiments described herein are merely intended to explain the invention, but not intended to limit the invention. In accordance with the purposes of this invention, as embodied and broadly described herein, this invention, in certain aspects, relates to methods and apparatus/systems for intraoperative assessment of parathyroid gland vascularity using laser speckle contrast imaging (LSCI) and applications of the same.

The LSCI technique analyzes the interference pattern produced when coherent light is incident on a surface.

Minute differences in path length created by the light waves scattering from different regions of the surface produce bright and dark spots of constructive and destructive interference respectively, termed as a speckle pattern. This speckle pattern fluctuates depending on how fast particles are moving within a few microns of the surface. Blurring of the speckle pattern occurs when the motion is fast relative to the integration time of the detector. Analyzing this spatial blurring provides contrast between regions of faster versus slower motion and forms the basis of LSCI [17]. This technique is sensitive to microvascular perfusion and has been employed in a variety of tissues where the vessels of interest are generally superficial, such as the retina, skin and brain [17]. Many of its applications have been in laboratory settings for investigating phenomena such as skin blood flow dynamics in response to external stimuli [18, 19], and cerebral blood flow in animal models of stroke [20]. Clinically, LSCI and similar techniques have been applied to monitoring Port Wine Stain laser therapy [21], correlating perfusion with healing time in burn wounds [22], and measuring cerebral blood flow in patients undergoing brain tumor resection [23]. However, there are no published reports on the application of LSCI or any other label-free optical method for assessing parathyroid gland viability during endocrine surgery. Parathyroid glands are densely packed with blood vessels, given that they secrete PTH to the entire body. Furthermore, their small size (3-8 mm [11]) makes many of these vessels superficial, making these glands suitable targets for assessment using LSCI.

Embodiments of this invention present the LSCI for real-time assessment of parathyroid viability. Taking an experienced surgeon's visual assessment as the gold standard, LSCI can be used to distinguish between well vascularized (n=32) and compromised (n=27) parathyroid glands during thyroid surgery with an accuracy of 91.5%. Ability to detect vascular compromise with LSCI was validated in parathyroidectomies. Results showed that this technique is able to detect parathyroid gland devascularization before it is visually apparent to the surgeon. Measurements can be performed in real-time and without the need to turn off operating room lights. LSCI shows promise as a real-time, contrast-free, objective method for helping reduce hypoparathyroidism after thyroid surgery.

One aspect of the invention relates to a method of using LSCI for intraoperative assessment of parathyroid gland viability in a surgery. The method includes diffusing a beam of light onto a tissue surface of a parathyroid gland of a patient to illuminate the tissue surface; acquiring images of the illuminated tissue surface, where each of the acquired images comprises a speckle pattern; and processing the acquired images to obtain speckle contrast images for the intraoperative assessment of parathyroid gland viability. In the speckle contrast images, a perfused parathyroid gland has low speckle contrast, and a devascularized parathyroid gland has high speckle contrast.

In one embodiment, the method further includes displaying the speckle contrast images of the parathyroid gland in real-time.

In one embodiment, the beam of light is emitted from a light source. In one embodiment, the light source comprises an infrared laser.

In one embodiment, said acquiring the images of the illuminated tissue surface is performed with a detector.

In one embodiment, the detector comprises a camera. In one embodiment, the camera comprises an infrared camera or a near-infrared camera. In one embodiment, the detector further comprises a focus tunable lens attached to the front end of the camera.

In one embodiment, said processing the acquired images comprises calculating a plurality of speckle contrasts from the acquired images of the parathyroid gland.

In one embodiment, said calculating plurality of speckle contrasts comprises defining a window with a number of pixels over which a speckle contrast is to be calculated; moving the window across the acquired image of the speckle pattern; and at each location, calculating the speckle contrast as a standard deviation of pixel intensity values as within the window divided by a mean intensity value $\langle I \rangle$ as follows:

$$K_s = \frac{\sigma_s}{\langle I \rangle}$$

where the resultant speckle contrast image has values that range from 0 to 1, with values closer to 0 representing regions of greater motion (perfusion) and 1 representing regions with no motion.

Another aspect of the invention relates to an apparatus (device/system) of using LSCI for intraoperative assessment of parathyroid gland viability in a surgery. In one embodiment, as shown in FIG. 1, the apparatus includes a light source (e.g., a 785 nm diode laser) for emitting a beam of light, and a diffuser (e.g., a lens tube having a biconvex lens) coupled to the light source for diffusing the beam of light onto a tissue surface of a parathyroid gland (e.g., object) of a patient to illuminate the tissue surface. The biconvex lens diffuses the beam of light to a spot with a diameter of D on the tissue surface at a distance of H from the edge of the biconvex lens. The light source is an infrared laser, or the like.

The apparatus also includes a detector (e.g., NIR camera) positioned above the tissue surface for acquiring images of the illuminated tissue surface. In one embodiment, the detector comprises a camera. The camera can be a charge-coupled device (CCD) camera and/or a complementary metal-oxide-semiconductor (CMOS) camera. In one embodiment, the camera comprises an infrared camera or a near-infrared (NIR) camera. In one embodiment, the detector further comprises a focus tunable lens (e.g., a zoom lens) attached to the front end of the camera.

The apparatus further includes a computer (controller) arranged to operate the detector to acquire the images of the illuminated tissue surface, receive the acquired images from the detector, and process the acquired images to obtain speckle contrast images for the intraoperative assessment of parathyroid gland viability. In the speckle contrast images, a perfused parathyroid gland has low speckle contrast, and a devascularized parathyroid gland has high speckle contrast.

The apparatus also includes a display for displaying the speckle contrast images of the parathyroid gland in real-time.

In addition, the apparatus includes a laser pointer arranged in relation to the detector such that its beam is co-localized with a center of the field of view of the detector at a distance.

In one embodiment, said processing the acquired images of the parathyroid gland by the controller is performed with calculating a plurality of speckle contrasts from the acquired images of the parathyroid gland.

In one embodiment, said calculating a plurality of speckle contrasts from the acquired images of the parathyroid gland is performed by defining a window with a number of pixels over which a speckle contrast is to be calculated; moving the window across the acquired image of the speckle pattern; and at each location, calculating the speckle contrast as a standard deviation of pixel intensity values as within the window divided by a mean intensity value ⟨I⟩ as follows:

$$K_s = \frac{\sigma_s}{\langle I \rangle}$$

where the resultant speckle contrast image has values that range from 0 to 1, with values closer to 0 representing regions of greater motion (perfusion) and 1 representing regions with no motion.

In certain aspects, this invention uses laser speckle imaging to provide a real-time non-invasive means to inform the surgeons whether or not a parathyroid gland is still being perfused and is therefore viable. During a thyroid or parathyroid surgery, the invented apparatus or device acquires and processes images of the parathyroid gland. The device comprises a 785 nm wavelength laser and a near-infrared camera with a zoom lens, positioned above the surgical filed via an articulated arm. The laser light is diffused onto the tissue surface and images are acquired by the camera. Images are acquired using a program developed on commercially available software, and processed to produce speckle contrast image through the lab-developed dynamic link library file written in C++. This allows the speckle contrast images to be displayed to the surgeon in real-time (as they are acquired). In these speckle contrast images, perfused (and therefore viable) parathyroid glands generally have low speckle contrast, while devascularized parathyroid glands have high speckle contrast.

The device and processing software have been proven feasible in a group of patients. Speckle contrast images of vascularized parathyroid glands and devascularized parathyroid glands are acquired during parathyroidectomy, where darker regions represent areas of greater blood flow and lighter regions represent areas of reduced blood flow. The speckle contrast images of parathyroid glands are compared against the surgeon's assessment of whether or not the gland was devascularized, where the confidence level of the surgeon were also recorded. For larger parathyroids the images agree 100% with the surgeon's assessment, however the device did not function as well for smaller (normal) glands. In certain embodiments, some modifications to the device is made to incorporated a zoom lens, which is now getting better agreement for smaller parathyroid glands.

Conventional laser speckle contrast imager appears less ergonomically suitable (more bulky) for use in the OR in the assessment of parathyroid glands than the invented LSCI device. According to the invention, the LSCI device can be combined with another lab-built device for detecting parathyroid gland using fluorescence, and marketed to endocrine surgeons. In addition, the invention allows for a more compact final product capable of assisting surgeons in first identifying parathyroid glands, and then assessing their viability.

These and other aspects of the present invention are further described in the following section. Without intending to limit the scope of the invention, further exemplary implementations of the present invention according to the embodiments of the present invention are given below. Note that titles or subtitles may be used in the examples for the convenience of a reader, which in no way should limit the scope of the invention. Moreover, certain theories are proposed and disclosed herein; however, in no way should they, whether they are right or wrong, limit the scope of the invention so long as the invention is practiced according to the invention without regard for any particular theory or scheme of action.

Example

Intraoperative Assessment of Parathyroid Viability Using Laser Speckle Contrast Imaging This exemplary example was performed in patients undergoing thyroidectomies and parathyroidectomies by measuring the speckle contrast of parathyroid glands in vivo. Performance of LSCI was evaluated in thyroidectomies, by grouping speckle contrast from normal functioning and compromised parathyroid glands according to the surgeon's classification. Validation was performed in parathyroidectomies, where the state of vascularity of the parathyroid gland was controlled in glands planned for excision. Results demonstrate the effectiveness of LSCI for parathyroid gland assessment.

Figure 2:
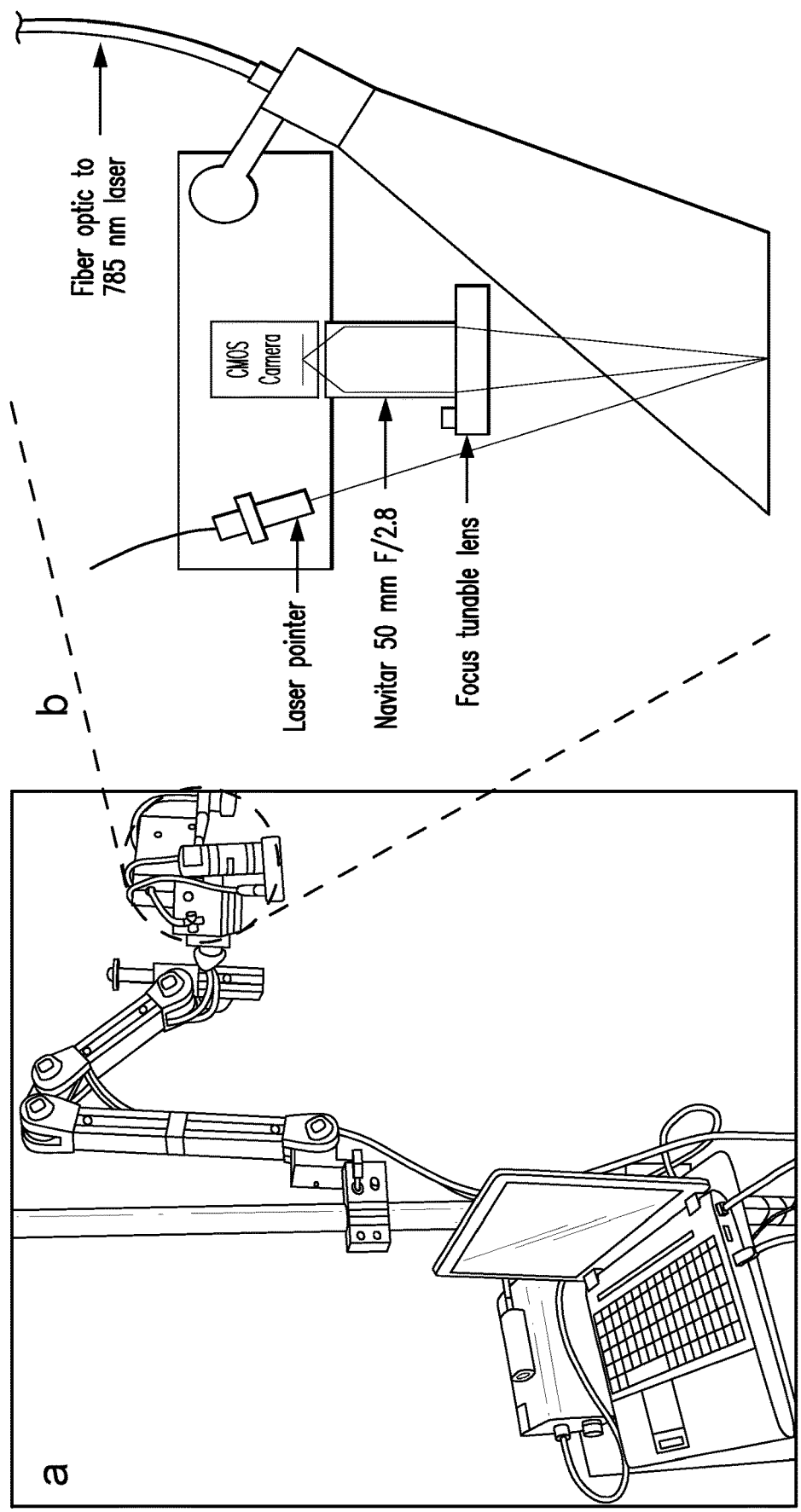
FIG. 2 shows an LSCI device, according to one embodiment of the invention, where (a) a picture of the device, and (b) a schematic of an imaging end (b) of the device.

Materials and Methods:

LSCI System Design:

An LSCI system, as shown in FIG. 2, which is operably the operating room (OR), was developed according to one embodiment of the invention. In the exemplary embodiment, the LSCI system is mounted on an articulated arm attached to a mobile cart. A 785 nm diode laser (Innovative Photonics Solutions, Monmouth Junction, N.J.) is coupled through a 400 µm fiber optic patch cord (Thorlabs, Newton, N.J.) to a lens tube containing a 75 mm focal length biconvex lens (Thorlabs, Newton, N.J.). This lens diverges (diffuses) the laser light to a spot of about 8 cm diameter at a distance of about 45 cm from the edge of the lens. The irradiance at the surface was measured to be about 0.6 mW/cm$^2$. A near-infrared optimized camera (acA1300-60gmNIR, Basler AG, Ahrensburg, Germany) captures the images, which are focused onto the camera sensor by an imaging lens system (Navitar 50 mm F/2.8, Navitar, Woburn, Mass.). Attached to the front end of the imaging lens system is a focus tunable lens (EL-16-40-TC-VIS-5D-M27, Optotune, Dietikon, Switzerland). This allows the images to be focused during each procedure from outside the sterile field as the height of the operating table may be slightly adjusted during surgery. The field of view of the camera was measured to be about 5 cm×6 cm. A 5 mW 660 nm laser pointer (DigiKey, Thief River Falls, Minn.) is attached such that its beam is co-localized with the center of the camera's field of view at a distance of 45 cm. The purpose of this laser pointer is to guide the surgeon in positioning the system above a parathyroid gland so that it is approximately in the center of the field of view. Images recorded by the camera are sent to a laptop computer for processing and display.

Ensuring Adequate Sampling of Speckle Pattern:

An important consideration when performing LSCI is that the speckle pattern must be adequately sampled. The smallest speckle should be at least twice the size of the sensor pixel in order to meet the Nyquist sampling criterion and avoid underestimating speckle contrast [25]. To test whether the invented LSCI system met this criterion, an optical tissue phantom made of polydimethylsiloxane (PDMS) with titanium dioxide to simulate tissue scattering (reduced scattering coefficient of 8 cm$^{-1}$) was illuminated and imaged with the LSCI device using different aperture sizes. The power spectrum was analyzed to ensure there was no aliasing. The iris size was set close to f/16 and locked in this position for the entire study. A well-defined energy band centered at the origin of the power spectrum confirmed no aliasing. Although larger apertures also had no aliasing, this aperture size was chosen because it also resulted in very little background from ambient lighting.

Patient Recruitment and Imaging Protocol:

This study was conducted in accordance with the Declaration of Helsinki and its amendments. The study was approved by the Vanderbilt University Medical Center (VUMC) Institutional Review Board (IRB). Patients undergoing partial or total thyroidectomy at the Vanderbilt University Medical Center were recruited and written informed consent was obtained from each patient (n=20) prior to participation.

Images of parathyroid glands were recorded during the course of surgery at the discretion of the surgeon. The surgeon first determined the state of vascularity of the gland based on visual inspection, and then positioned the LSCI device above the surgical field so that the laser pointer beam was on the parathyroid gland. With the camera integration time set to about 50 ms to allow imaging with the room lights on, white light images were initially acquired to identify the location of the parathyroid gland. The laser pointer was turned off and the integration time was then set to 5 ms for the rest of the image acquisitions. This integration time is within the range typically used for LSCI [17], and results in the room lights contributing very little signal to the image while effectively detecting the 785 nm speckle pattern. Next, the 785 nm laser was turned on and images were acquired and sent to the computer for real-time processing of speckle contrast images. Roughly fifteen seconds of acquisition were allowed for each gland to ensure that a sufficient number of images was obtained. The surgeon was blinded to all images during the surgery.

Validation of Technique:

Given that there is no gold standard for assessing parathyroid gland viability, validation of this technique was performed as follows. Patients undergoing parathyroidectomy at the VUMC were recruited and written informed consent obtained prior to participation following IRB approval. In parathyroidectomies, a diseased parathyroid gland is planned for removal. As part of standard procedure, the surgeon ligated blood supply to the diseased parathyroid gland prior to excision. This provides a controllable scenario for evaluating the capability of the device to detect parathyroid gland vascular compromise.

Speckle contrast images were acquired before and less than one minute after the surgeon ligated the blood supply to the gland, in preparation for removal. To confirm removal of the hyperactive parathyroid gland, intraoperative measurement of PTH was performed before and 10 minutes after excision of the gland. Changes in speckle contrast between the vascularized and ligated state were assessed.

Speckle Contrast Calculation:

The number of pixels over which spatial speckle contrast is calculated is important, with too few pixels resulting in inaccuracy in contrast estimation while too many pixels sacrificing spatial resolution. Calculating speckle contrast over a 5×5 or 7×7 pixel region is generally considered a good compromise [26]. In this exemplary embodiment, a 5×5 pixel window was used in calculating speckle contrast. The window is moved across the image of the acquired speckle pattern and at each location, the speckle contrast is calculated as the standard deviation of pixel intensity values within the window divided by the mean (Equation 1). The resultant speckle contrast image has values that range from 0 to 1, with values closer to 0 representing regions of greater motion (perfusion) and 1 representing regions with no motion. Image acquisition and display is performed through a custom LabVIEW program, while a custom dynamic link library file enables processing and display at about 10 frames per second.

$$K_s = \frac{\sigma_s}{\langle I \rangle} \quad (1)$$

Data Analysis:

Data was analyzed using MATLAB R2015a (The MathWorks Inc., Natick, Mass.). For each set of recordings on a single parathyroid gland, 20 speckle contrast images were averaged after acquisition to improve the spatial resolution of the final image. To correct for slight movement of the surgical field during recordings, an image registration algorithm was employed before averaging. Any image with sudden jerky motion (visually identified as a global sharp decrease in speckle contrast) was excluded from the averaging. The parathyroid gland was then demarcated using the "roipoly" function, avoiding bright spots caused by specular reflection, and the average speckle contrast within this region was calculated. In certain embodiments of the device, polarizers are used to reduce specular reflection. The data was then grouped into vascularized and compromised according to the surgeon's assessment of the gland. Compromised parathyroid glands were also further grouped into those that the surgeon decided to transplant and those that were left in place. Tests for statistical significance were performed using a two-sided two sample Student's t-test and p-values less than 0.01 were considered statistically significant.

Effect of Ambient Lighting on Speckle Contrast Images:

Performing measurements without the need to turn off the OR lights would minimize disruption to the surgical workflow. A microfluidic flow phantom made of PDMS and titanium dioxide to achieve a reduced scattering coefficient of 8 cm$^{-1}$ was used to evaluate the effect of ambient lighting on speckle contrast images in the laboratory. The device had a 400 μm channel through which a 1% Intralipid (Sigma-Aldrich, St. Louis, Mo.) solution was flowed. Images were acquired with the room lights on and then off, and 20 speckle contrast images were averaged for each condition.

For one patient undergoing parathyroidectomy, two sets of measurements on one parathyroid gland were obtained to determine the effect of the OR lights on speckle contrast images. The surgeon first positioned the device so the parathyroid gland was in the field of view. Images were recorded with the operating room lights on, but with the surgical lights above the operating table pointing away from the surgical field. Then, without moving the device, all operating room lights were turned off and another set of images were obtained. For each condition, 20 speckle contrast images were averaged and the same region of interest was used to calculate average parathyroid gland speckle contrast.

Results:

Device Design:

A portable, clinical LSCI device/system was developed and is shown in FIG. 2. In essence, the device includes a 785 nm coherent light source to diffuse light onto the surgical field, a near-infrared optimized camera to record the speckle pattern produced, and a computer to process and display images at 10 frames per second. The field of view was measured to be about 5 cm×6 cm at a distance of 45 cm above the operating table and the laser intensity at this distance was 0.6 mW/cm².

Figure 3:
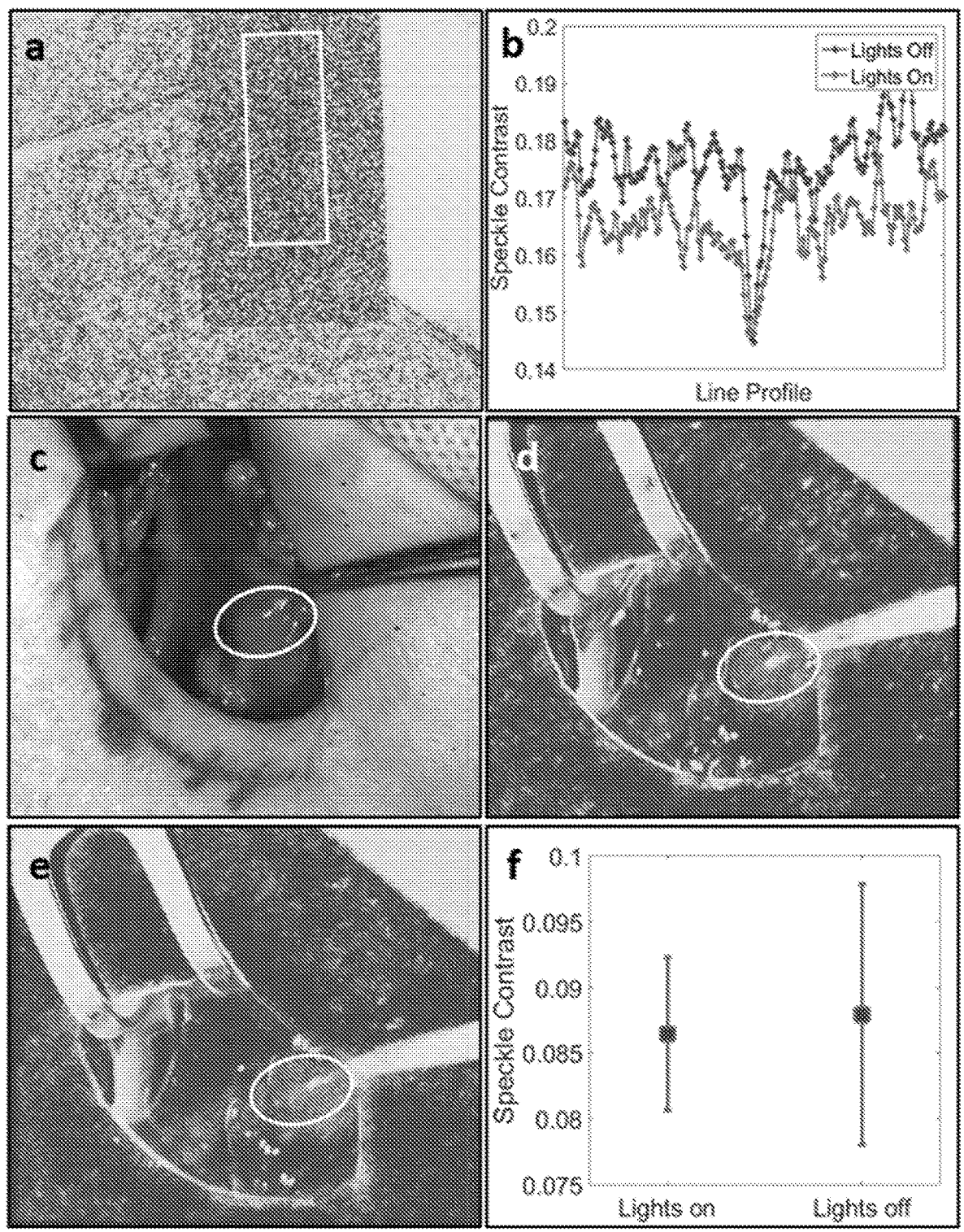
FIG. 3 shows speckle contrast images of a microfluidic flow phantom (a) and average line profile perpendicular to flow channel for both lighting conditions (b); white light image of surgical field with OR lights on (c); speckle contrast image with OR lights on (d); speckle contrast image with OR lights off (e); mean and standard deviation of speckle contrast within parathyroid for both cases (f). Parathyroid glands are indicated with white ellipses and the flow phantom region of interest is indicated with a white rectangle.

Effect of Ambient Lighting on Speckle Contrast Images:

Performing measurements without the need to turn off the operating room (OR) lights is essential so that any disruption to the surgical workflow is minimized. The effect of ambient lights on speckle contrast was evaluated in the laboratory on a microfluidic flow phantom with a 1% Intralipid solution flowing through its 400 µm channel (FIGS. 3a and 3b). A rectangular region of interest crossing the channel was selected and line profiles perpendicular to the channel within this region were averaged for both conditions, lights on and lights off. There was no significant difference in the decrease in speckle contrast when crossing the channel, using a two-sample Student's t-test (p=0.19).

To determine how room lights would affect LSCI data acquired in the operating room, the system was tested in vivo on a patient undergoing parathyroidectomy. One set of images was acquired with the room lights on and the surgical lights above the operating table pointed away from the surgical field, and another set with all lights off. For each condition, 20 speckle contrast images were averaged after acquisition and the same region of interest was used to calculate average parathyroid gland speckle contrast. There was a 1.7% decrease in the average speckle contrast value of the parathyroid gland when the OR lights were left on, compared to when they were off (FIGS. 3c-3f). This is to be expected since OR lights have a broad frequency spectrum [24] and therefore do not produce a speckle pattern. The uniform lighting fills in dark spots in the speckle pattern generated by the laser, thereby reducing the contrast. However, the magnitude of this decrease (about 0.002) was miniscule compared to the possible range of speckle contrast values (0 to 1). Additionally, this value is less than 2% of the range of average parathyroid gland speckle contrast obtained in this study. These results indicated that the performance of the LSCI system is not affected by ambient light and validates its application in the operating room with the OR lights on but pointed away from the patient during image acquisition.

Figure 4:
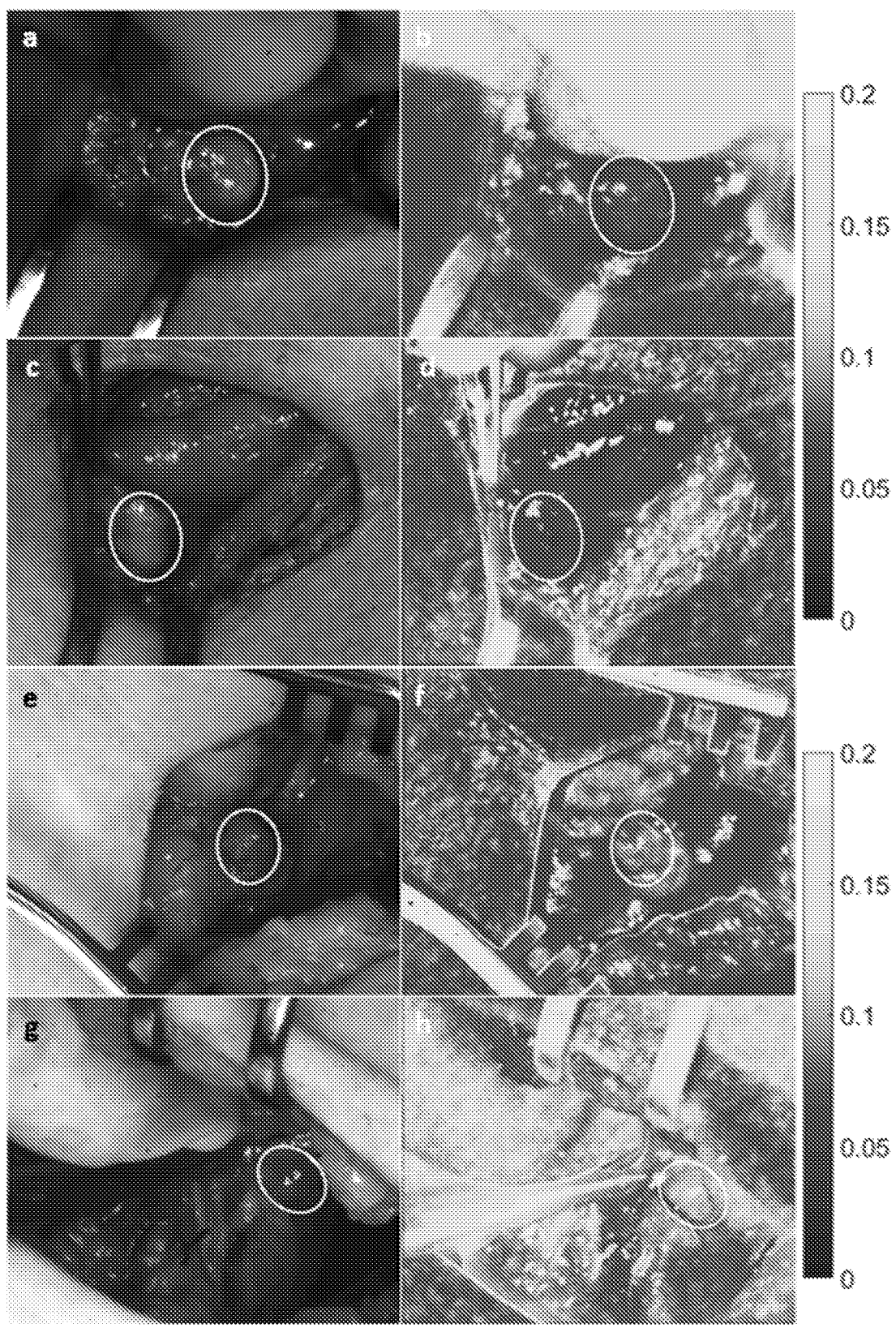
FIG. 4 shows images for two examples, each of vascularized (a-d) and compromised (e-h) parathyroid glands. Left column (a, c, e, g) shows white light images, with the corresponding speckle contrast images (b, d, f, h) in the right column.

Vascularized vs. Compromised Parathyroid Glands:

The LSCI system was tested in twenty patients undergoing thyroidectomy at Vanderbilt University Medical Center. Speckle contrast images of parathyroid glands were acquired during the course of surgery and at the discretion of the participating surgeon. The surgeon's visual assessment of the gland's viability (without input from speckle contrast images) was recorded at the time of image acquisition for each gland. FIG. 4 shows examples of parathyroid glands considered vascularized and compromised. The left column shows white light images of the surgical field, and the right column shows the corresponding speckle contrast image (average of 20 images). Parathyroid glands are indicated with a white ellipse. As these images show, parathyroid glands considered vascularized by the surgeon have lower speckle contrast than those considered to be compromised.

Figure 5:
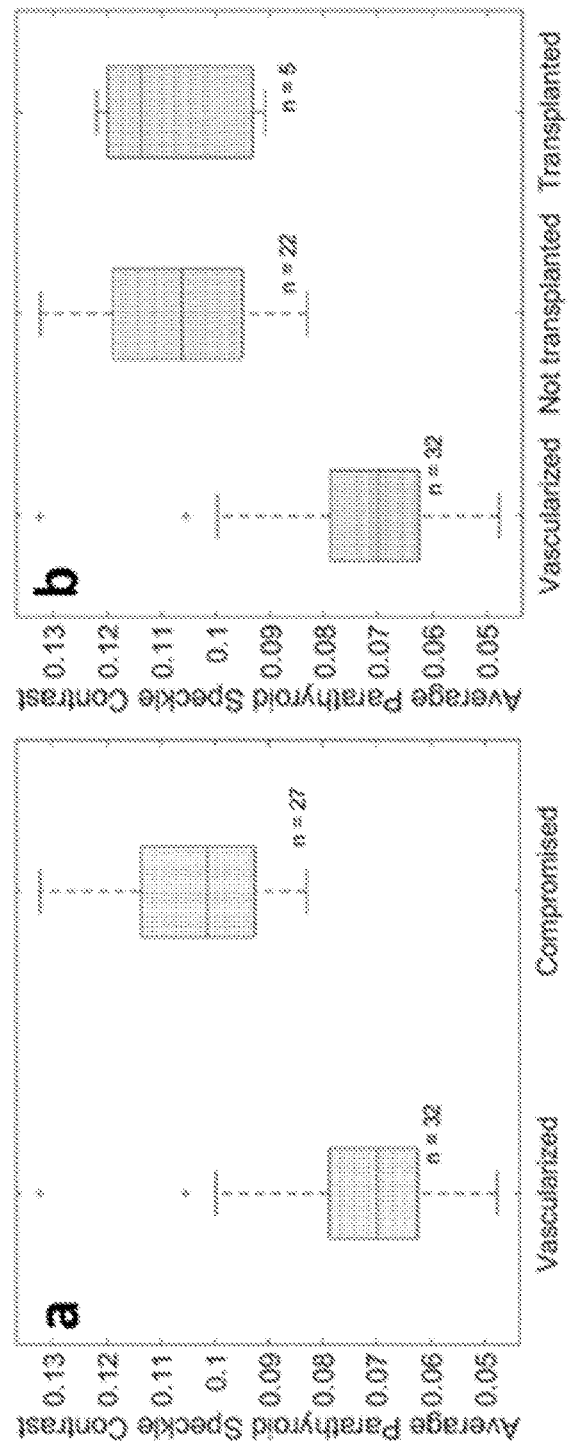
FIG. 5 shows an average parathyroid gland speckle contrast grouped according to surgeon's assessment. Speckle contrast is significantly lower (p<0.0001) for vascularized glands (a). Of the compromised glands only 5 required transplantation, however no significant difference was observed between this sub-group and the compromised glands that were left in place (b). Classifying parathyroid glands based on average speckle contrast generated an ROC curve with an area under the curve of 0.935, and an optimum point with sensitivity and specificity of 92.6% and 90.6% respectively (c).
Figure 5:
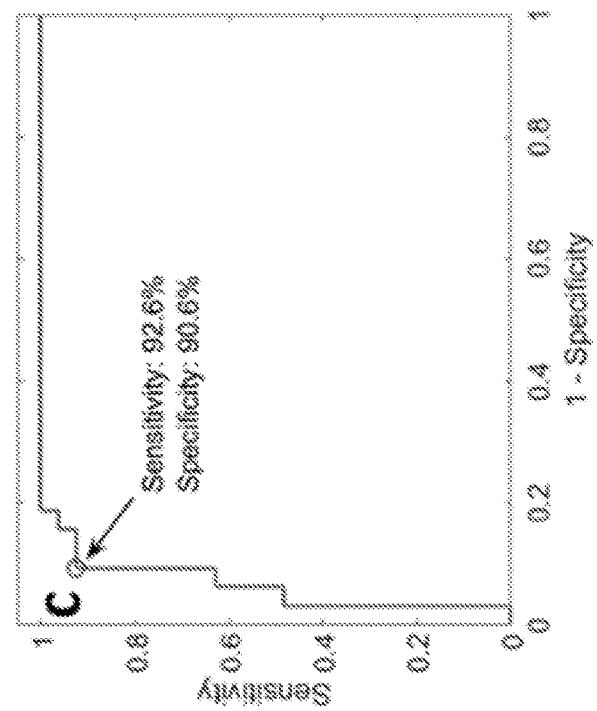

The average speckle contrast within each parathyroid gland was calculated, avoiding bright spots of specular reflection. This data was then grouped according to the surgeon's visual assessment of vascularity, which served as the gold standard. Using a two-sample two-sided Student's t-test, a statistically significant difference (p<0.0001) was observed in the speckle contrast between glands considered vascularized versus compromised as determined by the surgeon (FIG. 5a). Within the compromised group, there were 5 glands that were transplanted, and 22 others that the surgeon decided could be left in place without significant adverse effects to the patient. While the mean speckle contrast was higher in the transplanted group, this difference was not found to be significant using a two-sample t-test. These results are shown in FIG. 5b.

Using speckle contrast as a classifier to distinguish between the vascularized and compromised parathyroid glands, a receiver operating characteristic (ROC) curve was generated with an area under the curve of 0.935 (FIG. 5c). The optimum threshold for distinguishing between the two groups was found to be 0.09, which resulted in a sensitivity of 92.6% (25/27 compromised glands correctly identified) and a specificity of 90.6% (29/32 vascularized glands correctly identified). From this, the overall accuracy was calculated to be 91.5%.

Validation of Technique:

Given that there is no gold standard for assessing parathyroid gland viability and these normal functioning glands cannot be excised for histological validation without compromising patient care, validation of the LSCI system for this application was performed on eight patients undergoing parathyroidectomy, where a diseased parathyroid gland is planned for removal. As part of standard procedure, the surgeon ties off all blood supply to the gland prior to excision. This provides a controllable scenario for evaluating the capability of the device to detect when a parathyroid gland is compromised as well as to determine the detection limit (or time) of the system. To confirm removal of the hyperactive parathyroid gland, intraoperative measurement of PTH is routinely performed before and 10 minutes after excision of the gland.

Figure 6:
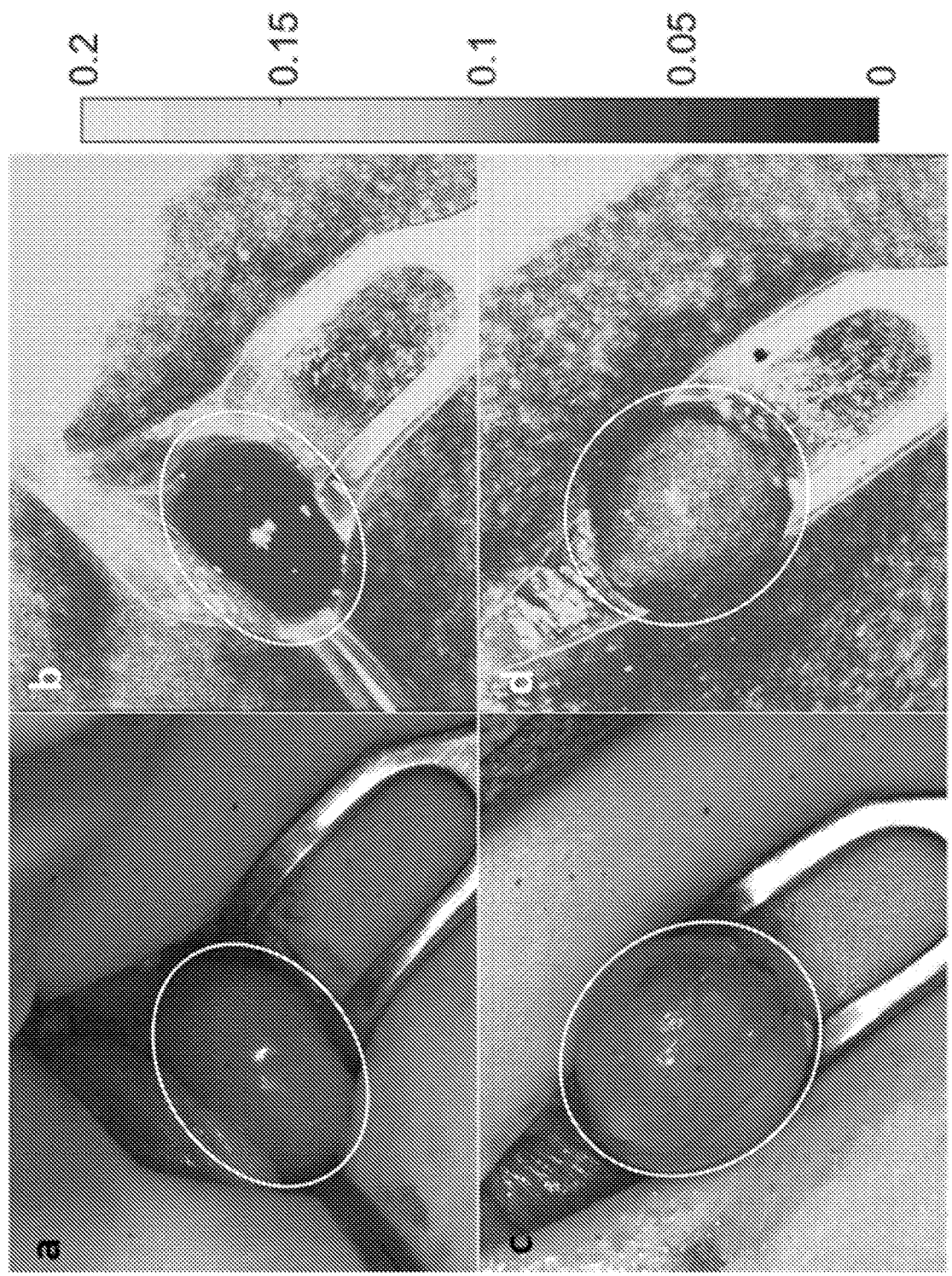
FIG. 6 shows changes in speckle contrast occurring seconds after blood supply ligation. A very noticeable change in speckle contrast (b, d) was observed in the same parathyroid gland seconds after tying off blood supply to the gland, however no such change was observed in white light images (a, c). Images (a) and (b) were taken before, while images (c) and (d) were taken about 30 seconds after ligation of the blood supply.

An example of a hypercellular diseased parathyroid gland marked for removal is shown in FIG. 6. Again, the left column shows white light images while the corresponding speckle contrast images are in the right column. Images on the top row are of the gland before the surgeon tied off the blood supply. Images on the bottom row were taken on average 30 seconds after the surgeon tied off the blood supply to the gland. According to the surgeon and as seen in the white light image, this gland did not appear visually different from its initial state. However, there is a clear change in the speckle contrast images. In all cases, speckle contrast increased by a minimum of 18% after the surgeon tied off the blood supply (data shown in Table I; mean increase of 0.043). Further, post-excision intraoperative PTH was also lower than pre-excision PTH, confirming removal of the diseased gland. PTH data was not acquired for two glands of patient 5 because removal of the first diseased gland resulted in PTH falling within the acceptable range (10-70 pg/mL) and all glands were diseased (Roche Elecsys 2010).

TABLE I

Summary of data from excised diseased parathyroid glands. In all cases there was a large increase in speckle contrast seconds after ligation of the blood supply to the gland. There was also a decrease in PTH related to the number of diseased glands removed. In patient 5, LSCI data was obtained from 3 glands that were excised, however PTH measurement was not performed after removal of glands 2 and 3.

| Patient No. | Pre-ligation speckle contrast | Post-ligation speckle contrast | Pre-excision [PTH] (pg/mL) | Post-excision [PTH] (pg/mL) |
|---|---|---|---|---|
| 1 | 0.076 | 0.126 | 86 | 26 |
| 2 | 0.057 | 0.094 | 142 | 34 |
| 3 | 0.062 | 0.131 | 172 | 32 |

TABLE I-continued

Summary of data from excised diseased parathyroid glands. In all cases there was a large increase in speckle contrast seconds after ligation of the blood supply to the gland. There was also a decrease in PTH related to the number of diseased glands removed. In patient 5, LSCI data was obtained from 3 glands that were excised, however PTH measurement was not performed after removal of glands 2 and 3.

| Patient No. | Pre-ligation speckle contrast | Post-ligation speckle contrast | Pre-excision [PTH] (pg/mL) | Post-excision [PTH] (pg/mL) |
| --- | --- | --- | --- | --- |
| 4 | 0.074 | 0.130 | 119 | 115 |
| 4 | 0.069 | 0.119 | 115 | 45 |
| 5 | 0.064 | 0.093 | 151 | 53 |
| 5 | 0.048 | 0.085 | 53 | N/A |
| 5 | 0.084 | 0.113 | N/A | N/A |
| 6 | 0.063 | 0.092 | 130 | 31 |
| 7 | 0.067 | 0.115 | 76 | 26 |

Discussions:

This exemplary embodiment of the invention demonstrates the capability of LSCI to intraoperatively distinguish between vascularized and compromised parathyroid glands. These measurements can be performed in real-time and with the operating room lights on, minimizing disruption to the surgical workflow. The average speckle contrast value of vascularized parathyroid glands was significantly lower than that of the compromised parathyroid glands, consistent with the understanding that reduced blood flow causes less blurring of the speckle pattern and therefore a higher speckle contrast [17]. Using the ROC curve in FIG. 5c, a speckle contrast value of about 0.09 was found to be optimal in distinguishing between the two groups with 91.5% accuracy. The ability of LSCI to accurately detect compromised vascularity in the parathyroid gland was validated in the parathyroidectomy cases. These images further show that this device is able to detect changes in speckle contrast within seconds of devascularization. This is much earlier than a surgeon would be able to identify based on visual inspection alone which relies on the gland turning dark with deoxygenated blood and losing turgor, a process which can take several minutes and is often missed. Unlike other techniques that have been used to assess parathyroid gland viability, LSCI can be performed non-invasively, with no risk of damage to the parathyroid gland by physical trauma, nor damage to any nearby tissues. It does not require administration of an exogenous contrast agent, which can take 1-2 minutes to achieve optimum circulation [16]. Additionally, multiple measurements can be made on the same gland without risk of toxicity. The device enables real-time assessment by processing and displaying speckle contrast images at 10 frames per second. The images shown in the disclosure were created after acquisition by averaging individual frames in order to improve spatial resolution. However, quantitative information on a region of interest can also be displayed in real-time if desired as this information is generated concurrently with imaging. This technique can be performed with the room lights on, only requiring that the lights above the operating table be pointed away from the surgical field.

The biggest challenge facing this study is the fact that the current gold standard for assessing parathyroid gland viability intraoperatively relies on the surgeon's experience which is highly subjective. The participated surgeon has multiple years of experience in this field and is therefore more likely than not to provide accurate assessments. However, thyroidectomies are routinely performed by general surgeons and residents, and a higher error rate is likely, indicating the need for objective assessment of parathyroid viability. These results demonstrate that LSCI has the potential to become the gold standard in this field.

In the absence of an objective gold standard to validate the performance of this device, paired measurements were made in parathyroidectomy cases where the state of vascularity was controlled. It should be noted that the PTH measurements made after excision of the glands are not meant to directly correlate with speckle contrast values but are simply to confirm that the excised tissues are diseased parathyroid glands. A more robust validation method would be to measure PTH after tying off the gland but before excision. However, this was not feasible as it takes about 5-10 minutes for PTH levels to stabilize to a new value and such a procedure would extend OR time and lead to added risk for the patient.

Figure 7:
FIG. 7 shows LSCI detects vascular compromise in healthy parathyroid gland before it is visually apparent. White light image of a parathyroid gland initially thought well vascularized (a) did not agree with speckle contrast image (b). After 15 minutes, this gland was re-evaluated as devascularized (c) and transplanted. Speckle contrast image (d) supported this assessment.

While this device performed with high accuracy in distinguishing between vascularized and compromised parathyroid glands in thyroidectomies, there were 5 instances of disagreement with the surgeon. One case shed light on a possible reason for this disagreement. This particular parathyroid gland was evaluated by the surgeon to be initially well vascularized, however its high speckle contrast value suggested otherwise as observed in FIG. 7b. After 15 minutes, the surgeon re-evaluated this gland as devascularized and transplanted it, with speckle contrast images agreeing with this assessment (FIG. 7d). This case further demonstrates the ability of LSCI to detect vascular compromise before it is visually apparent to the surgeon.

An interesting observation was that of the 27 glands the surgeon considered to have suffered vascular compromise, only 5 were autotransplanted. The rest were considered capable of recovery. However, no significant differences in speckle contrast were observed between these two groups (though the small sample size for the transplanted group will make any differences difficult to identify). This warrants further investigation with a larger study to identify what is truly viable. Future studies will additionally acquire pre- and post-surgery PTH measurements in patients with autotransplanted and intact parathyroid glands so that patient outcome may be correlated with speckle contrast images. This will enable answering questions such as: "Should all glands with speckle contrast above a given threshold be autotransplanted in order to avoid hypoparathyroidism?", and/or, "Is it safe to leave suspicious-looking glands in place if at least one parathyroid has speckle contrast below this threshold?"

It should be noted that LSCI senses motion, therefore these measurements are highly susceptible to random movement of the surgical field caused by the patient's breathing and movement of the hands holding retractors to expose the surgical field. Image registration was used to align images prior to averaging, however this does not avoid the artificial decrease in speckle contrast introduced to a single frame by such motion. For reference, the average speckle contrast of an excised parathyroid gland placed on a stable surface in the same operating room was measured to be 0.2, whereas the highest value obtained in vivo was about 0.13. In spite of this unavoidable source of error, very distinct differences in speckle contrast were obtained as demonstrated by the parathyroidectomy data (Table I). To improve the accuracy of the final image, any image with jerky motion (visually identified as a global sharp decrease in speckle contrast) was excluded from the averaging. This was done manually due to the rarity of the event. In the future, should it be required, an algorithm could be employed to automate this process and reject speckle contrast images with values a specified percentage below the mean. Regardless of these limitations, this study clearly shows the applicability of LSCI as a real-time, contrast-free and objective guidance tool for assessing parathyroid gland viability intraoperatively. It will be of particular benefit to less experienced surgeons and residents, and could reduce hospitalization and long-term medication costs associated with post-surgical hypoparathyroidism. This device could also have applicability for other clinical procedures where there is the need to non-invasively investigate the presence of tissue perfusion.

In sum, the invention presents LSCI as a potential real-time, non-invasive, contrast-free and objective tool for guiding surgeons during thyroid surgeries to assess the viability of parathyroid glands. The device according to embodiments of the invention can provide this information to surgeons with minimal disruption to the surgical workflow, and can detect vascular compromise in its early stages before it becomes evident to the surgeon's eye. This tool can therefore significantly minimize post-surgical hypoparathyroidism and its consequent morbidities and costs.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LISTING OF REFERENCES

[1]. American Thyroid Association. General Information/Press Room. (2017). at <http://www.thyroid.org/media-main/about-hypothyroidism/>

[2]. Sun, G. H., DeMonner, S. & Davis, M. M. Epidemiological and Economic Trends in Inpatient and Outpatient Thyroidectomy in the United States, 1996-2006. *Thyroid* 23, 727-733 (2013).

[3]. Rafferty, M. A. et al. Completion Thyroidectomy Versus Total Thyroidectomy: Is There a Difference in Complication Rates? An Analysis of 350 Patients. *J. Am. Coll. Surg.* 205, 602-607 (2007).

[4]. Schwartz, A. E. & Friedman, E. W. Preservation of the parathyroid glands in total thyroidectomy. *Surg. Gynecol. Obstet.* 165, 327-32 (1987).

[5]. Ritter, K., Elfenbein, D., Schneider, D. F., Chen, H. & Sippel, R. S. Hypoparathyroidism after total thyroidectomy: incidence and resolution. *J. Surg. Res.* 197, 348-53 (2015).

[6]. Demeester-Mirkine, N., Hooghe, L., Van Geertruyden, J. & De Maertelaer, V. Hypocalcemia after thyroidectomy. *Arch. Surg.* 127, 854-8 (1992).

[7]. Pattou, F. et al. Hypocalcemia following Thyroid Surgery: Incidence and Prediction of Outcome. *World J. Surg* 22, 718-724 (1998).

[8]. McHenry, C. R., Speroff, T., Wentworth, D. & Murphy, T. Risk factors for postthyroidectomy hypocalcemia. *Surgery* 116, 641-7-8 (1994).

[9]. Zahedi Niaki, N. et al. The Cost of Prolonged Hospitalization due to Postthyroidectomy Hypocalcemia: A Case-Control Study. *Adv. Endocrinol.* 2014, 1-4 (2014).

[10]. Naveh-Many, T. *Molecular Biology of the Parathyroid.* (Kluwer Academic/Plenum Publishers, 2005). at <http://web.b.ebscohost.com.proxy.library.vanderbilt.edu/ehost/ebookviewer/ebook/bm xlYmtfXzEyNTkwNF9fQU41?sid=0747ff07-a77e-43ea-9efe-aa979596f166@sessionmgr2&vid=0&format=EB&lpid=lp_x&rid=0>

[11]. Mohebati, A. & Shaha, A. R. Anatomy of thyroid and parathyroid glands and neurovascular relations. *Clin. Anat.* 25, 19-31 (2012).

[12]. Lo, C. Y. et al. Parathyroid Autotransplantation During Thyroidectomy. *Arch. Surg.* 136, 1381 (2001).

[13]. Sierra, M. et al. Prospective biochemical and scintigraphic evaluation of autografted normal parathyroid glands in patients undergoing thyroid operations. *Surgery* 124, 1005-10 (1998).

[14]. Kuriloff, D. B. & Kizhner, V. Parathyroid gland preservation and selective autotransplantation utilizing topical lidocaine in total thyroidectomy. *Laryngoscope* 120, 1342-1344 (2010).

[15]. Ezzat, W. et al. Intraoperative parathyroid hormone as an indicator for parathyroid gland preservation in thyroid surgery. *Swiss Med. Wkly.* (2011). doi:10.4414/smw.2011.13299

[16]. Fortuny, J. V. et al. Parathyroid gland angiography with indocyanine green fluorescence to predict parathyroid function after thyroid surgery. *Br. J. Surg.* 103, 537-543 (2016).

[17]. Boas, D. A. & Dunn, A. K. Laser speckle contrast imaging in biomedical optics. *J. Biomed. Opt.* 15, 11109 (2010).

[18]. Choi, B., Kang, N. M. & Nelson, J. S. Laser speckle imaging for monitoring blood flow dynamics in the in vivo rodent dorsal skin fold model. *Microvasc. Res.* 68, 143-6 (2004).

[19]. Iredahl, F., Löfberg, A., Sjöberg, F., Farnebo, S. & Tesselaar, E. Non-Invasive Measurement of Skin Microvascular Response during Pharmacological and Physiological Provocations. *PLoS One* 10, e0133760 (2015).

[20]. Dunn, A. K., Bolay, H., Moskowitz, M. A. & Boas, D. A. Dynamic Imaging of Cerebral Blood Flow Using Laser Speckle. *J. Cereb. Blood Flow Metab.* 21, 195-201 (2001).

[21]. Huang, Y.-C., Ringold, T. L., Nelson, J. S. & Choi, B. Noninvasive blood flow imaging for real-time feedback during laser therapy of port wine stain birthmarks. *Lasers Surg. Med.* 40, 167-173 (2008).

[22]. Mirdell, R., Iredahl, F., Sj?berg, F., Farnebo, S. & Tesselaar, E. Microvascular blood flow in scalds in children and its relation to duration of wound healing: A study using laser speckle contrast imaging. *Burns* 42, 648-654 (2016).

[23]. Richards, L. M. et al. Intraoperative multi-exposure speckle imaging of cerebral blood flow. *J. Cereb. Blood Flow Metab.* 0271678X1668698 (2017). doi:10.1177/0271678X16686987

[24]. Sexton, K. J., Zhao, Y., Davis, S. C., Jiang, S. & Pogue, B. W. Optimization of fluorescent imaging in the operating room through pulsed acquisition and gating to ambient background cycling. *Biomed. Opt. Express* 8, 2635 (2017).

[25]. Kirkpatrick, S. J., Duncan, D. D. & Wells-Gray, E. M. Detrimental effects of speckle-pixel size matching in laser speckle contrast imaging. *Opt. Lett.* 33, 2886 (2008).

[26]. Briers, D. et al. Laser speckle contrast imaging: theoretical and practical limitations. *J. Biomed. Opt.* 18, 66018 (2013).

What is claimed is:

1. A method for intraoperative assessment of parathyroid gland viability in a surgery, comprising:
    diffusing a beam of light onto a tissue surface of a parathyroid gland of a patient to illuminate the tissue surface;
    acquiring images of the illuminated tissue surface, wherein each of the acquired images comprises a speckle pattern; and
    processing the acquired images to obtain speckle contrast images for the intraoperative assessment of parathyroid gland viability.

2. The method of claim 1, wherein the beam of light is emitted from a light source.

3. The method of claim 2, wherein the light source comprises an infrared laser.

4. The method of claim 1, wherein said acquiring the images of the illuminated tissue surface is performed with a detector.

5. The method of claim 4, wherein the detector comprises a camera.

6. The method of claim 5, wherein the camera comprises an infrared camera or a near-infrared camera.

7. The method of claim 5, wherein the detector further comprises a focus tunable lens attached to the front end of the camera.

8. The method of claim 1, wherein in the speckle contrast images, a perfused parathyroid gland has low speckle contrast, and a devascularized parathyroid gland has high speckle contrast.

9. The method of claim 1, wherein said processing the acquired images comprises calculating a plurality of speckle contrasts from the acquired images of the parathyroid gland.

10. The method of claim 9, wherein said calculating plurality of speckle contrasts comprises:
    defining a window with a number of pixels over which a speckle contrast is to be calculated;
    moving the window across the acquired image of the speckle pattern; and
    at each location, calculating the speckle contrast as a standard deviation of pixel intensity values $\sigma_s$ within the window divided by a mean intensity value $\langle I \rangle$ as follows:

$$K_s = \frac{\sigma_s}{\langle I \rangle}$$

wherein the resultant speckle contrast image has values that range from 0 to 1, with values closer to 0 representing regions of greater motion (perfusion) and 1 representing regions with no motion.

11. The method of claim 1, further comprising:
    displaying the speckle contrast images of the parathyroid gland in real-time.

12. The apparatus of claim 1, further comprising a display for displaying the speckle contrast images of the parathyroid gland in real-time.

13. An apparatus for intraoperative assessment of parathyroid gland viability in a surgery, comprising:
    a light source for emitting a beam of light;
    a diffuser coupled to the light source for diffusing the beam of light onto a tissue surface of a parathyroid gland of a patient to illuminate the tissue surface;
    a detector for acquiring images of the illuminated tissue surface, wherein each of the acquired images comprises a speckle pattern; and
    a controller arranged to operate the detector to acquire the images of the illuminated tissue surface, receive the acquired images from the detector, and process the acquired images to obtain speckle contrast images for the intraoperative assessment of parathyroid gland viability.

14. The apparatus of claim 13, wherein the light source comprises an infrared laser.

15. The apparatus of claim 13, wherein the diffuser comprises a biconvex lens.

16. The apparatus of claim 13, wherein the detector comprises a camera.

17. The apparatus of claim 16, wherein the camera comprises an infrared camera or a near-infrared camera.

18. The apparatus of claim 16, wherein the detector further comprises a focus tunable lens attached to the front end of the camera.

19. The apparatus of claim 13, further comprising a laser pointer arranged in relation to the detector such that its beam is co-localized with a center of the field of view of the detector at a distance.

20. The apparatus of claim 13, wherein in the speckle contrast images, a perfused parathyroid gland has low speckle contrast, and a devascularized parathyroid gland has high speckle contrast.

21. The apparatus of claim 13, wherein said processing the acquired images of the parathyroid gland by the controller is performed with calculating a plurality of speckle contrasts from the acquired images of the parathyroid gland.

22. The apparatus of claim 21, wherein said calculating a plurality of speckle contrasts from the acquired images of the parathyroid gland is performed with:
    defining a window with a number of pixels over which a speckle contrast is to be calculated;
    moving the window across the acquired image of the speckle pattern; and
    at each location, calculating the speckle contrast as a standard deviation of pixel intensity values $\sigma_s$ within the window divided by a mean intensity value $\langle I \rangle$ as follows:

$$K_s = \frac{\sigma_s}{\langle I \rangle}$$

wherein the resultant speckle contrast image has values that range from 0 to 1, with values closer to 0 representing regions of greater motion (perfusion) and 1 representing regions with no motion.

* * * * *